(12) United States Patent
Bendel et al.

(10) Patent No.: US 11,534,507 B2
(45) Date of Patent: Dec. 27, 2022

(54) REMOVAL DEVICE BY WHICH LIQUIDS FOR PRODUCING PARENTERAL DRUGS ARE REMOVED FROM A CONDUIT SYSTEM

(71) Applicant: Hoffmann-La Roche Inc., Little Falls, NJ (US)

(72) Inventors: Volker Bendel, Mannheim (DE); Matthias Laika, Mannheim (DE); Wolfgang Rieger, Mannheim (DE)

(73) Assignee: Hoffmann-La Roche Inc., Little Falls, NJ (US)

(*) Notice: Subject to any disclaimer, the term of this patent is extended or adjusted under 35 U.S.C. 154(b) by 332 days.

(21) Appl. No.: 16/658,995

(22) Filed: Oct. 21, 2019

(65) Prior Publication Data
US 2020/0046863 A1  Feb. 13, 2020

Related U.S. Application Data

(63) Continuation of application No. PCT/EP2018/060403, filed on Apr. 24, 2018.

(30) Foreign Application Priority Data

Apr. 24, 2017 (EP) .................................. 17167704

(51) Int. Cl.
*A61L 2/07* (2006.01)
*E03C 1/02* (2006.01)

(52) U.S. Cl.
CPC .................. *A61L 2/07* (2013.01); *E03C 1/02* (2013.01); *A61L 2202/121* (2013.01); *A61L 2202/123* (2013.01); *E03C 2201/40* (2013.01)

(58) Field of Classification Search
CPC ............................ A61L 2/07; A61L 2202/123
See application file for complete search history.

(56) References Cited

U.S. PATENT DOCUMENTS 3,870,033 A    3/1975  Faylor et al.
4,547,339 A *  10/1985 McClure .................. A61L 2/04
                                              134/22.15
(Continued)

FOREIGN PATENT DOCUMENTS

CN    205549223 U    9/2016
DE       2755155 A1    6/1979
(Continued)

OTHER PUBLICATIONS

Bobe et al., Anforderungen an Werkstoffe und Werkstoffoberflächen bezüglich Reinigbarkeit und Beständigkeit, Chemie Ingenieur Technik, Nov. 1, 2006, pp. 1615-1622, vol. 78.
(Continued)

*Primary Examiner* — Timothy C Cleveland
(74) *Attorney, Agent, or Firm* — Bose McKinney & Evans LLP

(57) ABSTRACT

A removal device for removing at least one low-germ liquid from a conduit system is disclosed. The removal device comprises at least one removal connection piece. The removal device further comprises at least one coupling bend, which is detachably connected to the removal connection piece. At least one tube end of the removal connection piece protrudes into an interior of the coupling bend and is sterilizable with pure steam on its inner face, its outer face and its end face within the coupling bend.

11 Claims, 4 Drawing Sheets

(56) References Cited

U.S. PATENT DOCUMENTS

| | | | |
|---|---|---|---|
| 5,290,442 A | 3/1994 | Clack | |
| 6,457,497 B1 | 10/2002 | Adriansens et al. | |
| 9,522,818 B2 * | 12/2016 | Clüsserath | B67C 3/225 |
| 2005/0025671 A1 * | 2/2005 | Kral | A61L 2/28 |
| | | | 422/62 |
| 2006/0186137 A1 | 8/2006 | Till | |
| 2015/0013832 A1 | 1/2015 | Riggio | |

FOREIGN PATENT DOCUMENTS

| DE | 3238434 A1 | 4/1984 |
|---|---|---|
| DE | 102005023391 A1 | 11/2006 |
| EP | 0487214 A1 | 5/1992 |
| EP | 1852131 A1 | 11/2007 |
| JP | 2000-126276 A | 5/2000 |
| JP | 2002-534329 A | 10/2002 |
| JP | 2011-046387 A | 3/2011 |
| WO | WO 0156613 A2 | 8/2001 |
| WO | WO 03029721 A1 | 4/2003 |
| WO | WO 2005016814 A1 | 2/2005 |
| WO | WO 2012066626 A1 | 5/2012 |

OTHER PUBLICATIONS

English Translation of the International Search Report and Written Opinion, PCT/EP2018/060403, dated Nov. 22, 2018, 23 pages.
English Translation of the International Preliminary Report on Patentability, PCT/EP2018/060403, dated Nov. 7, 2019, 22 pages.
Gereinigtes Wasser Aqua Purificata, Ph. Eur. 8th edition, 2014, pp. 5248-5257, vol. 3.

* cited by examiner

REMOVAL DEVICE BY WHICH LIQUIDS FOR PRODUCING PARENTERAL DRUGS ARE REMOVED FROM A CONDUIT SYSTEM

RELATED APPLICATIONS

This application is a continuation of PCT/EP2018/060403, filed Apr. 24, 2018, which claims priority to EP 17 167 704.0, filed Apr. 24, 2017, the entire disclosures of both of which are hereby incorporated herein by reference.

BACKGROUND

This disclosure relates to a removal device by which low-germ liquids, in particular pharmaceutical water of injection quality or of lower quality, are removed from a conduit system. This disclosure moreover relates to a conduit system for making available low-germ liquid, in particular pharmaceutical water, to a method by which low-germ liquid, in particular pharmaceutical water, is removed from a conduit system, and to a use of the removal device according to the disclosure. The devices and methods according to the present disclosure can be used in particular in the pharmaceutical industry, for example, for the production of infusion or injection solutions. The devices and methods according to the present disclosure can be used in particular for water for injection (WFI), highly purified water (HPW) or also generally for pure water and ultrapure water. It is possible in particular to use water of the qualities WFI, HPW or AP (aqua purificata) according to the European Pharmacopeia, for example, according to Ph. Eur. 8th edition, volume 3, pages 5248-5257. Other fields of use are also possible.

The provision of low-germ liquids, in particular of sterile liquids, is essential in many technological and scientific fields. Without excluding further possible fields of use, embodiments are described below with regard to making available sterile water for injection (WFI). Besides this, however, there are many other possible applications in which sterile liquids are used, for example, in laboratory diagnostics or in biochemical research.

In the production of parenteral drugs, i.e., infusion or injection solutions, it is customary to use water, also referred to as water for injection or WFI. To produce this water, various preparation techniques are used, often in combination, in particular distillation methods, reverse osmosis or ultrafiltration. The water is generally stored in tanks, pumped around at regular intervals and made available at the place of use by way of suitable conduit systems.

DE 27 55 155 A1 discloses a device for cleaning dispensing systems having at least one compensator tap. The device is characterized by a storage container for a cleaning liquid with at least one outflow nozzle and with a connecting tube to the outlet of the compensator tap, and by a restrictor element which is attachable to the end of the tap line directed away from the compensator tap.

Furthermore, WO 2005/016814 A1 describes a dispensing system for beverages, particularly beer, and a method for cleaning the system. The dispensing system contains a beverage tank, a tap, which is located above the beverage tank and is situated at a distance therefrom, and a beverage line whose first, upper end is connected to the tap and whose second, lower end is connected to the beverage tank. Moreover, a cleaning system is provided for introducing a cleaning agent into the beverage line. The cleaning system has, at the first end of the beverage line, an inlet, and, at the second end of the beverage line, an outlet for the cleaning agent.

Moreover, WO 2012/066626 A1 discloses a dispenser comprising a cold water plumbing system for supplying chilled water, and a hot water plumbing system for supplying heated water, wherein both systems are connected to one filling port by a three-way valve, which is a valve having three ports. The dispenser is characterized by a sterilization process which is performed by passing water through the cold water plumbing system and the hot water plumbing system by the three-way valve, and by circulating hot water through both of the plumbing systems using a convection phenomenon caused by the difference in water temperatures. The dispenser is capable of performing thermal sterilization with the aid of a very simple structure in which only a three-way valve is additionally used. A cold water filling port, in which the propagation of bacteria most likely occurs, can be sterilized by heat, using the filling port both for cold water and hot water.

Furthermore, DE 10 2005 023391 A1 describes a device for thermal disinfection of structural units of a respiratory system that carry respiratory gas, comprising a carrier unit which can be coupled to the structural unit and contains at least one air treatment component for the disinfection of the structural unit, an air inlet opening and an air outlet opening, such that the structural unit, in the disinfection mode, is acted on by an air stream heated to a predefined minimum temperature, wherein the air inlet opening of the carrier unit can be attached to an existing air outlet opening of the structural unit, and the air outlet opening of the carrier unit can be attached to an existing air inlet opening of the structural unit, and the structural unit has at least one air treatment component, such that in the disinfection mode the heated air circulates in a circuit formed by the carrier unit and the structural unit.

Moreover, DE 32 38 434 A1 discloses a method and a device for the heat treatment of goods, in which the goods to be treated are guided axially through an annular chamber whose outer and inner boundary surfaces are heated under thermostatic control. The inner boundary surface is formed by an inner body which is configured as a worm and can be driven by motor, while the outer boundary surface is composed of a double-jacket tube which is provided on the inner face with volutes. The outer tube, insulated on its outer surface, is provided with steam admission and condensate discharge ports attached at the interspace between the jacket surfaces. The rotating inner body is provided with a condensate lifting device.

Furthermore, Bobe et al. ("Anforderungen an Werkstoffe und Werkstoffoberflächen bezüglich Reinigbarkeit und Beständigkeit", CHEMIE INGENIEUR TECHNIK, vol. 78, no. 11, Nov. 1, 2006 (2006-11-01), pages 1615-1622, XP055423970, Weinheim; DE, ISSN: 0009-286X, DOI: 10.1002/C.200600095) describe the current state of research as regards the effects of material surfaces on cleanability. They moreover discuss causes of possible corrosion damage on non-stainless steels, including the possibilities of preventing damage, and the field of use of EPDM as an elastomeric sealing material.

Moreover, WO 01/56613 A2 discloses a sterile water generator which, on demand, generates a stream of sterile water. A water heater heats incoming, unsterile water to a sufficient temperature to achieve sterilization of the water. The sterile water is then passed through a heat exchanger which transfers excess heat from the sterile water to the incoming water. This reduces the energy consumption of the water heater and reduces the temperature of the sterile water that is ready for use. The sterile water is delivered to a site, at which the water is to be used, through a sterile delivery path in order to avoid contamination of the water. A first portion of the delivery path is pre-sterilized by flowing steam or hot water, which is produced by the water heater, along the delivery path. A second portion of the delivery path is sterilized by an antimicrobial liquid. The first and second portions of the delivery path comprise at least one common section.

Furthermore, EP 1 852 131 A1 describes a closed water dispenser comprising a water dispense system with a cold water reservoir for dispensing chilled water from an outlet and a hot water reservoir for dispensing hot water from an outlet. The cold water reservoir comprises an inlet, wherein the inlet is releasably connectable to an inverted bottle for replacing dispensed water. The system is periodically disinfected to kill bacteria in the system by temporarily connecting the outlets and circulating steam or hot water generated in the hot water reservoir.

A technical challenge in the preparation of liquids, in particular WFI, is generally that the removal point at which the WFI is taken from the conduit system should be low in germs. Otherwise, germs and pollutants can enter the conduit system and the sample via the removal point. In many laboratories, the removal point, for example, a tap or connection piece, is therefore sterilized before and/or after the removal, for example, by means of a burner. However, a disadvantage of such methods is that they require attentiveness on the part of the operating personnel. Carelessness in some cases affects the entire conduit system. Moreover, conventional techniques for sterilizing the removal point, for example, the use of a burner, place a strain on the removal point and are generally difficult to automate.

SUMMARY

A removal device, a conduit system, a method and a use which at least largely avoid the disadvantages of known devices and methods is disclosed herein. In particular, it is taught herein that at least one low-germ liquid can be safely removed from a conduit system in a simple, user-friendly and yet reliable manner, at least largely avoiding microbial contamination of the conduit system.

Hereinafter, the terms "have", "comprise" or "include" or any grammatical deviations therefrom are used in a non-exclusive way. Accordingly, these terms can refer either to situations in which, besides the features introduced by these terms, no further features are present, or to situations in which one or more further features are present. For example, the expression "A has B", "A comprises B" or "A includes B" may refer both to the situation in which no further element aside from B is provided in A (that is to say to a situation in which A is composed exclusively of B) and to the situation in which, in addition to B, one or more further elements are provided in A, for example, element C, elements C and D, or even further elements.

Furthermore, it is pointed out that the terms "at least one" and "one or more" and grammatical modifications of these terms, if they are used in association with one or more elements or features and are intended to express the fact that the element or feature can be provided singly or multiply, in general are used only once, for example, when the feature or element is introduced for the first time. When the feature or element is subsequently mentioned again, the corresponding term "at least one" or "one or more" is generally no longer used, without excluding the possibility that the feature or element can be provided singly or multiply.

Further, it should be understood that all terms used throughout this disclosure and claims, regardless of whether said terms are preceded by the phrases "one or more, "at least one, or the like, should not receive a singular interpretation unless it is made explicit herein. That is, all terms used in this disclosure and claims should generally be interpreted to mean "one or more" or "at least one."

Furthermore, hereinafter the terms "preferably", "in particular", "for example" or similar terms are used in conjunction with optional features, without alternative embodiments thereby being restricted. In this regard, features introduced by these terms are optional features, and there is no intention to restrict the scope of protection of the claims, and in particular of the independent claims, by these features. In this regard, this disclosure, as will be recognized by a person skilled in the art, can also be carried out using other configurations. Similarly, features introduced by "in one embodiment of the disclosure" or "in one exemplary embodiment of the disclosure" are to be understood to be optional features, without this being intended to restrict alternative refinements or the scope of protection of the independent claims. Furthermore, all possibilities of combining the features introduced by these introductory expressions with other features, whether optional or non-optional features, are intended to remain unaffected by said introductory expressions.

In a first aspect of the present disclosure, a removal device for removing at least one low-germ liquid from a conduit system is proposed. A "removal device" is to be understood in principle as any device that allows a liquid to be removed from a storage container or from a conduit.

In the context of the present disclosure, a "low-germ liquid" is to be understood generally as a liquid that has been subjected to a germ reduction process. The low-germ liquid can in particular have a count of less than 100 germs per 100 ml, in particular a count of less than 50 germs per 100 ml or even a count of less than 10 germs per 100 ml. In particular, the low-germ liquid can be water, in particular water of the qualities WFI, HPW or AP according to the European Pharmacopeia, for example, according to Ph. Eur., 8th edition, volume 3, pages 5248-5257. However, other liquids, in particular liquids not containing water, can in principle be used.

In the context of the present disclosure, a "conduit system" is to be understood as an arrangement with one or more conduits and/or one or more storage devices, through which a low-germ liquid can be conveyed or in which a low-germ liquid can be stored. In particular, the conduit system can be configured to at least largely prevent entry of germs into a liquid located in the conduit or in the storage device.

The removal device comprises at least one removal connection piece. In the context of the present disclosure, a "removal connection piece" is to be understood as an end of a pipe which is open or can be opened. In particular, as is described in more detail below, the removal connection piece can comprise a tube portion which at one end is connected directly or indirectly to the conduit system and at another end is opened or can be opened. The tube portion can, for example, be connected to the conduit system via at least one valve, such that a free flow of the low-germ liquid out of the conduit system through the removal connection piece can be prevented and can then be enabled only by the valve.

The removal device further comprises at least one coupling bend. The coupling bend is detachably connected to the removal connection piece. At least one tube end of the removal connection piece protrudes into an interior of the coupling bend. The tube end of the removal connection piece protruding into the removal connection piece can be sterilized in the coupling bend at its inner face, its outer face and its end face by pure steam, sterilizing steam or pharmaceutical ultrapure steam.

In the context of the present disclosure, a "coupling bend" is to be understood generally as a covering which can receive part of the removal connection piece, in the present case in particular the tube end, and can close the latter off from the outside. The coupling bend can in particular have at least one cavity into which the tube end can protrude in order to be flushed there by pure steam and disinfected. The cavity can in particular be dimensioned in such a way that the outer face, the end face and the inner face of the tube end are exposed and are freely accessible to the steam. As is explained in more detail below, the coupling bend can in particular likewise be configured with an at least partially tubular shape, with an internal diameter that is greater than the tube end of the removal connection piece, such that the tube end can be inserted into the tubular coupling bend. The tube of the coupling bend can be straight or preferably also curved. The coupling bend can likewise have a pipe connector, with an end that can be pushed onto the tube end of the removal connection piece. However, other configurations are also possible in principle.

A "detachable connection" is to be understood generally as a connection that is reversible. In particular, it can be a force-fit connection between the removal connection piece and the coupling bend. This force-fit connection can, for example, comprise at least one screw connection. To remove the liquid, the coupling bend can, for example, be detached from the removal connection piece such that the low-germ liquid can flow out of the removal connection piece as soon as a valve is opened. Otherwise, if low-germ liquid is not to be removed, the coupling bend can be fitted onto the tube end of the removal connection piece, such that the tube end is protected by the coupling bend against contamination.

An arrangement in which the tube end of the removal connection piece in the coupling bend can be sterilized with pure steam at its inner face, its outer face and its end face is to be understood as an arrangement in which the tube end is received freely in the coupling bend in such a way that pure steam, which is conveyed through the removal connection piece itself and/or through the coupling bend to the tube end, can pass freely to the inner face, the outer face and the end face of the tube end in order to kill germs there.

If no low-germ liquid is removed, it is thereby possible overall on the one hand to effectively avoid contamination of the removal connection piece by means of the coupling bend. Before or also after removal of the low-germ liquid, the tube end of the coupling bend can be sterilized with pure steam, without operating personnel coming into contact with the pure steam. This method can also be automated.

The tube end of the removal connection piece can in particular be surrounded annularly by an inner wall of the coupling bend, in particular if the coupling bend is itself tubular. The tube end can in this way be received in a manner spaced apart from the inner wall of the coupling bend, such that an annular gap forms between the inner wall and the tube end, into which annular gap the pure steam can penetrate. The annular gap can in particular have a gap thickness of 0.2 mm to 5 mm, preferably of 0.5 mm to 3 mm, and particularly preferably of 0.7 mm to 1 mm. However, other dimensions are also possible in principle.

As has been stated above, the removal connection piece can in particular be tubular, for example, at least partially cylindrical with a circular, oval or polygonal cross section, and it can, for example, have an internal diameter, if appropriate also an equivalent internal diameter. The internal diameter can in particular be 3 mm to 40 mm, in particular 10 mm to 20 mm. However, other dimensions are also possible in principle.

As has likewise already been stated above, the coupling bend can in particular also be tubular and have an internal diameter. The internal diameter of the coupling bend can in particular be 4 mm to 50 mm, in particular 11 mm to 42 mm. However, other dimensions are also possible in principle. In particular, the internal diameter of the coupling bend can have a greater internal diameter than the removal connection piece, at least in a region into which the tube end of the removal connection piece protrudes.

Since sterilization of the tube end with pure steam preferably takes place in the coupling bend, it is advantageous if the coupling bend is at least partially thermally insulated so that operating personnel are not injured when detaching the coupling bend from the removal connection piece. Accordingly, the coupling bend can be configured at least partially with a double wall. Alternatively or in addition to a double-walled configuration, however, other thermal insulations are also conceivable. However, a double-walled configuration can be easily realized and is in particular easy to clean. The double-walled configuration can in particular be such that a cavity is provided between two walls of the coupling bend, which cavity is preferably completely closed off such that no germs can enter said cavity.

The coupling bend can in particular have a double-walled configuration at least in a region into which the tube end of the removal connection piece protrudes. The coupling bend can be double-walled in the whole region into which the tube end of the removal connection piece protrudes, or only in a part of this region.

The double-walled configuration can in particular be generated by means of at least one outer sleeve, with an internal diameter greater than an external diameter of the coupling bend, being pushed onto the coupling bend. The coupling bend can thus be configured wholly or partially as a double tube, wherein an insulating annular gap can form between the tubes. The outer sleeve, i.e., the outer tube, can in this case be welded to the coupling bend, in particular to an inner tube.

The tube end of the removal connection piece can in particular protrude into the interior of the coupling bend by at least 10 mm, preferably by at least 20 mm. The tube end of the removal connection piece can in particular protrude into the interior of the coupling bend by at least 10 mm to 50 mm.

The removal connection piece can in particular be L-shaped. The coupling bend can also be L-shaped. One end of the L of the removal connection piece can, for example, be connected directly or indirectly to the conduit system, and the other end of the L of the removal connection piece can be connected to the coupling bend. Accordingly, one end of the L of the coupling bend can be connected to the removal connection piece. Another end of the L of the coupling bend can, for example, be connected directly or indirectly to an outflow. The removal device as a whole, with the removal connection piece and the coupling bend in a connected state, can thus have a U-shaped configuration with an angular or rounded U. In this way, for example, the removal device can be secured with the two ends of the U to a housing or to a wall.

An end face of the tube end of the removal connection piece can in particular be inclined with respect to a tube axis of the tube end. This beveled tube end can promote dripping of low-germ liquid, such that, for example, no drops of liquid remain at the tip of the tube end. In particular, the removal device can be mounted in such a way that the tip of the tube end points downward. An opened end of the coupling bend, which receives the tube end, can accordingly point upward.

The coupling bend can in particular be configured as a tube portion, wherein a first opening of the tube portion receives the tube end of the removal connection piece, and wherein a second opening of the tube portion can be subjected to pure steam, such that pure steam can pass through the tube portion from the second opening to the first opening and can there sterilize the tube end of the removal connection piece. The tube portion can in particular be bent in an L shape, with an angular or rounded L.

The coupling bend can in particular be connected to the removal connection piece via at least one force-fit and/or form-fit connection. In particular, the coupling bend can be detachably connected to the removal connection piece via at least one screw connection. For example, the screw connection can comprise at least one combination chosen from the group consisting of: an outer thread fixed to the coupling bend and a union nut arranged on the removal connection piece; an outer thread arranged on the removal connection piece and a union nut arranged on the coupling bend. The part of the combination of the removal device that carries the union nut can, for example, have a collar or a flange on which the union nut engages when it is screwed onto the outer thread of the respective other part.

The removal device can in particular be produced wholly or partially, in particular at the tube end, from steel, in particular from stainless steel. Steel and in particular stainless steel are particularly easy to clean and to disinfect, and they largely prevent contamination from occurring.

The removal device can in particular be configured wholly or partially, in particular at the tube end, with a very low surface roughness, so as to offer the least possible surface of attack for contamination. It is thus advantageous if at least the tube end of the removal connection piece has a surface roughness RMS of 0.1 to 2.0 micrometers, in particular of 0.2 to 0.6 micrometer, and particularly preferably of 0.4 micrometer or less.

Furthermore, the removal device can have at least one electrical contact, connected to the coupling bend, for connection to a control unit (also referred to herein as a "controller") and for detecting a state in which the coupling bend is connected to the removal connection piece. For example, the electrical contact can be connected rigidly to the coupling bend, wherein an arrangement of the removal device relative to the controller can be such that the electrical contact is connected to the controller only in a state when the coupling bend is connected to the removal connection piece. In this way, for example, the controller can prevent pure steam from being conveyed into the removal device when the removal connection piece is not fitted on the tube end. It is thus possible to prevent operating personnel from being injured by pure steam.

In a further aspect of the present disclosure, a conduit system for making available at least one low-germ liquid is proposed. The conduit system comprises at least one pipe system for the low-germ liquid. A "pipe system" is generally to be understood here as an arrangement with one or more pipes and/or one or more storage devices through which one or more liquids can be conveyed and/or in which one or more liquids can be stored. The conduit system further comprises at least one removal device according to this disclosure, for example, according to one or more of the above-described configurations and/or according to one or more of the configurations described in detail below. The removal device is connected to the pipe system, in particular in such a way that a fluidic connection exists between the pipe system and the removal device and/or in such a way that the removal device is integrated into the pipe system. The conduit system can comprise one or more removal devices, such that low-germ liquid can be removed from the pipe system at one or more removal points.

The conduit system can moreover have at least one container for receiving the low-germ liquid. The container can in particular be connected to the pipe system. The container can, for example, be configured in such a way that low-germ liquid is pumped continuously through this container. For example, at least one feed, for example, at least one spray nozzle, can be arranged at an upper end of the container and conveys low-germ liquid into the container, and an outflow through which low-germ liquid is removed from the container can be arranged at a lower end of the container. For example, the low-germ liquid can be pumped in the circulation through the pipe system, including the container. In particular, the pipe system can be of an annular configuration and can have at least one pump, which pump is designed to pump the low-germ liquid in a circulation through the pipe system and the container.

As has been stated above, the at least one removal device can be fluidically connected to the pipe system, for example, by means of the removal device being integrated directly into the pipe system or by means of a fluidic connection to the pipe system. The pipe system can in particular have at least one branch. The branch can be connected to the removal device. The branch can, for example, comprise at least one tube portion which at one end is connected directly or indirectly to the pipe system, for example, via a T-piece or a multi-way valve, and which at another end is connected directly or indirectly to the removal device. In particular, at least one valve can be provided between the branch and the removal device. This can be a two-way valve or also a multi-way valve or also, for example, simply a shut-off valve.

As has been stated above, the conduit system can comprise, besides the pipe system, one or more further components, which can be fluidic or also non-fluidic. In particular, one or more mechanical components or electronic components can be included. Thus, the conduit system can in particular also have at least one control unit, which can assume one or more controlling and/or regulating tasks. In particular, the control unit can be connectable to the coupling bend via at least one electrical contact and can be designed to detect whether the coupling bend is connected to the removal connection piece. As has been described above, the control unit can accordingly also be designed in particular to make pure steam available only when the coupling bend is connected to the removal connection piece and otherwise to prevent pure steam from being made available. For example, the control unit can actuate one or more valves which can enable the pure steam to act on the tube end of the removal connection piece. As has been stated above, it is thus possible, by means of the control unit, for example, to prevent operating personnel from being injured by pure steam when the coupling bend is detached from the removal connection piece.

Accordingly, at least one feed for pure steam can be arranged, for example, between the branch and the removal device, such that pure steam can be conveyed from the feed, through the removal connection piece and into the coupling bend, in order there to sterilize the tube end of the removal connection piece. The feed for the pure steam can in particular be closable with at least one valve. Alternatively or in addition, however, a feed for pure steam can also be arranged in at least one further location. For example, at least one feed for pure steam can be provided between an outflow and the coupling bend.

The coupling bend can in particular be connected to at least one outflow at an end directed away from the removal connection piece. At least one valve can in particular be provided between the coupling bend and the outflow. As has been stated above, at least one feed for pure steam can moreover be arranged between the coupling bend and the outflow. Furthermore, at least one condensate discharge can be provided between the coupling bend and the outflow, in particular between the at least one valve and the outflow.

In a further aspect of the present disclosure, a method for removing at least one low-germ liquid from a conduit system is proposed. The method uses the conduit system according to the present disclosure, and therefore, in respect of possible configurations, reference can be made to the above description, and also to the illustrative embodiments described below. The method comprises the following steps, which are preferably carried out in the sequence indicated. However, another sequence is also possible in principle, and also a method in which one or more of the method steps are carried out in a temporally overlapping manner or simultaneously or are also repeated once or several times. The method can comprise additional steps not mentioned.

The method comprises the following steps:
a) making available a conduit system according to one of the preceding embodiments relating to a conduit system;
b) introducing pure steam into the coupling bend and sterilizing the tube end of the removal connection piece in the interior of the coupling bend by flushing the pure steam around the tube end;
c) releasing and detaching the coupling bend from the removal connection piece; and
d) removing the low-germ liquid from the removal connection piece.

In the context of the present disclosure, "pure steam" is to be understood in principle as any desired steam, in particular water vapor. The steam can in particular have a defined quality. For example, the pure steam can be steam that is filtered, for example, with a filter pore size ≤10 micrometers or ≤4 micrometers. Alternatively or in addition, the pure steam can be steam of the low-germ liquid itself, i.e., the low-germ liquid in a gaseous state, for example, water of the quality WFI, HPW or AP in steam form. The pure steam can in particular be one or more of the following types of steam: pure steam as defined, e.g., in the US Pharmacopeia; sterilizing steam as defined, e.g., in DIN 58950 part 7; pharmaceutical ultrapure steam as defined, e.g., in DIN 58950 part 7. The steam can in particular have a higher temperature than the boiling temperature of the underlying liquid. It can in particular be steam, for example, water vapor having a temperature >100° C., in particular a temperature ≥121° C. For example, the pure steam can have temperatures of from 121° C. to ca. 140° C.

In a further aspect of the present disclosure, a use of a removal device according to the present disclosure for removing at least one low-germ liquid from a conduit system is proposed. The low-germ liquid can in particular be or comprise water for injection.

The proposed devices and the proposed method have many advantages over known devices and methods. In particular, the problem outlined above, namely the tube end of a removal device being exposed to the risk of contamination during removal of low-germ liquid, can be solved in a simple but reliable manner. Manual heating of the tube end, for example, by a user with a burner can be avoided. In particular, through the use of pure steam, in combination with the sterilization of the whole tube end by said pure steam, it is possible for germs to be efficiently killed off at the tube end before or also after removal, and this procedure can also be automated. Accordingly, the whole method can be controlled, for example, by a control unit. It is in this way possible to effectively reduce the influence of human action and in particular of carelessness, which could otherwise lead to microbial contamination of the entire conduit system, in particular of the entire conduit system for ultrapure water. At the same time, through the use of the coupling bend, it is possible to prevent the operating personnel from being jeopardized by the pure steam. It will be noted that, alternatively or additionally to pure steam, it is also possible to use other sterilizing media, for example, other sterilizing gases. These can be aspirated, for example, through the coupling bend, before the coupling bend is detached.

In summary, in the context of the present disclosure, the following embodiments are particularly preferred:

Embodiment 1: A removal device for removing at least one low-germ liquid from a conduit system, comprising at least one removal connection piece, further comprising at least one coupling bend, wherein the coupling bend is detachably connected to the removal connection piece, wherein at least one tube end of the removal connection piece protrudes into an interior of the coupling bend and is sterilizable with pure steam on its inner face, its outer face and its end face within the coupling bend.

Embodiment 2: A removal device according to the preceding embodiment, wherein the tube end of the removal connection piece is surrounded annularly by an inner wall of the coupling bend, wherein the tube end is spaced apart from the inner wall, such that an annular gap forms between the inner wall and the tube end, into which annular gap the pure steam can penetrate.

Embodiment 3: A removal device according to the preceding embodiment, wherein the annular gap has a gap thickness of 0.2 mm to 5 mm, preferably of 0.5 mm to 3 mm, and particularly preferably of 0.7 mm to 1 mm.

Embodiment 4: A removal device according to one of the preceding embodiments, wherein the removal connection piece is of annular configuration and has an internal diameter.

Embodiment 5: A removal device according to the preceding embodiment, wherein the internal diameter is 3 mm to 40 mm, in particular 10 mm to 20 mm.

Embodiment 6: A removal device according to one of the preceding two embodiments, wherein the coupling bend is of tubular configuration and has an internal diameter.

Embodiment 7: A removal device according to the preceding embodiment, wherein the internal diameter of the coupling bend is 4 mm to 50 mm, in particular 11 mm to 42 mm.

Embodiment 8: A removal device according to one of the preceding two embodiments, wherein the internal diameter of the coupling bend, at least in a region into which the tube end of the removal connection piece protrudes, has a greater internal diameter than the removal connection piece.

Embodiment 9: A removal device according to one of the preceding embodiments, wherein the coupling bend is configured at least partially with a double wall.

Embodiment 10: A removal device according to the preceding embodiment, wherein the coupling bend has a double-walled configuration at least in a region into which the tube end of the removal connection piece protrudes.

Embodiment 11: A removal device according to one of the preceding two embodiments, wherein the double-walled configuration is generated by means of at least one outer sleeve, with an internal diameter greater than an external diameter of the coupling bend, being pushed onto the coupling bend.

Embodiment 12: A removal device according to the preceding embodiment, wherein the outer sleeve is welded to the coupling bend.

Embodiment 13: A removal device according to one of the preceding embodiments, wherein the tube end of the removal connection piece protrudes into the interior of the coupling bend by at least 10 mm, preferably by at least 20 mm.

Embodiment 14: A removal device according to one of the preceding embodiments, wherein the tube end of the removal connection piece protrudes into the interior of the coupling bend by at least 10 mm to 50 mm.

Embodiment 15: A removal connection piece according to one of the preceding embodiments, wherein the removal connection piece is L-shaped, and wherein the coupling bend is L-shaped, such that the removal device as a whole, with the removal connection piece and the coupling bend in a connected state, has a U-shaped configuration.

Embodiment 16: A removal device according to one of the preceding embodiments, wherein the end face of the tube end of the removal connection piece is inclined with respect to a tube axis of the tube end.

Embodiment 17: A removal device according to one of the preceding embodiments, wherein the coupling bend is configured as a tube portion, wherein a first opening of the tube portion receives the tube end of the removal connection piece, and wherein a second opening of the tube portion can be subjected to pure steam, such that pure steam can pass through the tube portion from the second opening to the first opening and can there sterilize the tube end of the removal connection piece.

Embodiment 18: A removal device according to the preceding embodiment, wherein the tube portion is bent in an L shape.

Embodiment 19: A removal device according to one of the preceding embodiments, wherein the coupling bend is detachably connected to the removal connection piece via a screw connection.

Embodiment 20: A removal device according to the preceding embodiment, wherein the screw connection comprises at least one combination chosen from the group consisting of: an outer thread fixed to the coupling bend and a union nut arranged on the removal connection piece; an outer thread arranged on the removal connection piece and a union nut arranged on the coupling bend.

Embodiment 21: A removal device according to one of the preceding embodiments, wherein the removal device is produced wholly or partially from steel, in particular from stainless steel.

Embodiment 22: A removal device according to one of the preceding embodiments, wherein the tube end of the removal connection piece has a surface roughness RMS of 0.1 to 2.0 micrometers, in particular of 0.2 to 0.6 micrometer, and particularly preferably of 0.4 micrometer.

Embodiment 23: A removal device according to one of the preceding embodiments, wherein the removal device moreover has an electrical contact, connected to the coupling bend, for connection to a control unit and for detecting a state in which the coupling bend is connected to the removal connection piece.

Embodiment 24: A conduit system for making available at least one low-germ liquid, comprising at least one pipe system for the low-germ liquid, further comprising at least one removal device according to one of the preceding embodiments, wherein the removal device is connected to the pipe system.

Embodiment 25: A conduit system according to the preceding embodiment, wherein the conduit system moreover has at least one container for receiving the low-germ liquid, wherein the container is connected to the pipe system.

Embodiment 26: A conduit system according to the preceding embodiment, wherein the pipe system is of an annular configuration and has at least one pump, wherein the pump is designed to pump the low-germ liquid in a circulation through the pipe system and the container.

Embodiment 27: A conduit system according to one of the preceding embodiments relating to a conduit system, wherein the pipe system has at least one branch, wherein the branch is connected to the removal device.

Embodiment 28: A conduit system according to the preceding embodiment, wherein at least one valve is provided between the branch and the removal device.

Embodiment 29: A conduit system according to one of the preceding two embodiments, wherein at least one feed for pure steam is arranged between the branch and the removal device, such that pure steam is conveyable from the feed through the removal connection piece into the coupling bend, in order there to sterilize the tube end of the removal connection piece.

Embodiment 30: A conduit system according to the preceding embodiment, wherein the feed for the pure steam is closable with at least one valve.

Embodiment 31: A conduit system according to one of the preceding embodiments relating to a conduit system, wherein the conduit system moreover has at least one control unit, wherein the control unit is connectable to the coupling bend via at least one electrical contact and is designed to detect whether the coupling bend is connected to the removal connection piece, wherein the control unit is moreover designed to make pure steam available only when the coupling bend is connected to the removal connection piece and otherwise to prevent pure steam from being made available.

Embodiment 32: A conduit system according to one of the preceding embodiments relating to a conduit system, wherein the coupling bend is connected to at least one outflow at an end directed away from the removal connection piece.

Embodiment 33: A conduit system according to the preceding embodiment, wherein at least one valve is provided between the coupling bend and the outflow.

Embodiment 34: A conduit system according to one of the preceding two embodiments, wherein at least one condensate discharge is provided between the coupling bend and the outflow, in particular between the at least one valve and the outflow.

Embodiment 35: A method for removing at least one low-germ liquid from a conduit system, in particular a conduit system for ultrapure water, comprising the following steps:

a) making available a conduit system according to one of the preceding embodiments relating to a conduit system;

b) introducing pure steam into the coupling bend and sterilizing the tube end of the removal connection piece in the interior of the coupling bend by flushing the pure steam around the tube end;

c) releasing and detaching the coupling bend from the removal connection piece; and d) removing the low-germ liquid from the removal connection piece.

Embodiment 36: The method according to the preceding embodiment, wherein the pure steam has a temperature of 121° C. to 140° C.

Embodiment 37: A use of a removal device according to one of the preceding embodiments relating to a removal device, for removing at least one low-germ liquid from a conduit system, in particular from a conduit system for ultrapure water.

Embodiment 38: The use according to the preceding embodiment, wherein the low-germ liquid comprises water for injection purposes.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

FIGS. 1 to 4 show examples of a conduit system 110 for making available at least one low-germ liquid, and a removal device 112 for removing at least one low-germ liquid from the conduit system 110. The low-germ liquid can in particular be water for injection, i.e., water for injection purposes. Accordingly, the abbreviation WFI is also generally used hereinbelow when referring to the low-germ liquid.

Figure 1:
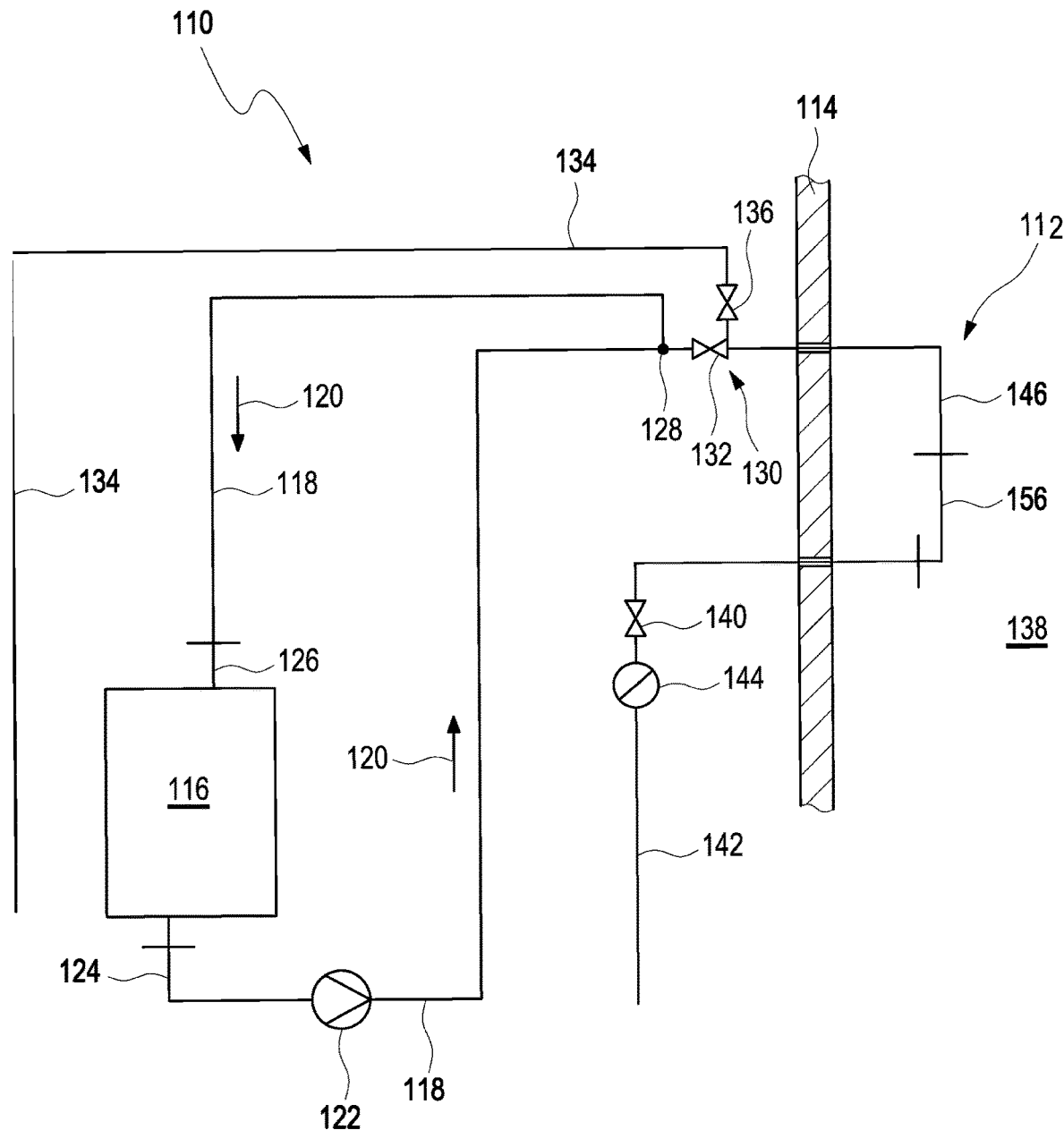
FIG. 1 shows a schematic view of an illustrative embodiment of a conduit system with a removal device.
Figure 2:
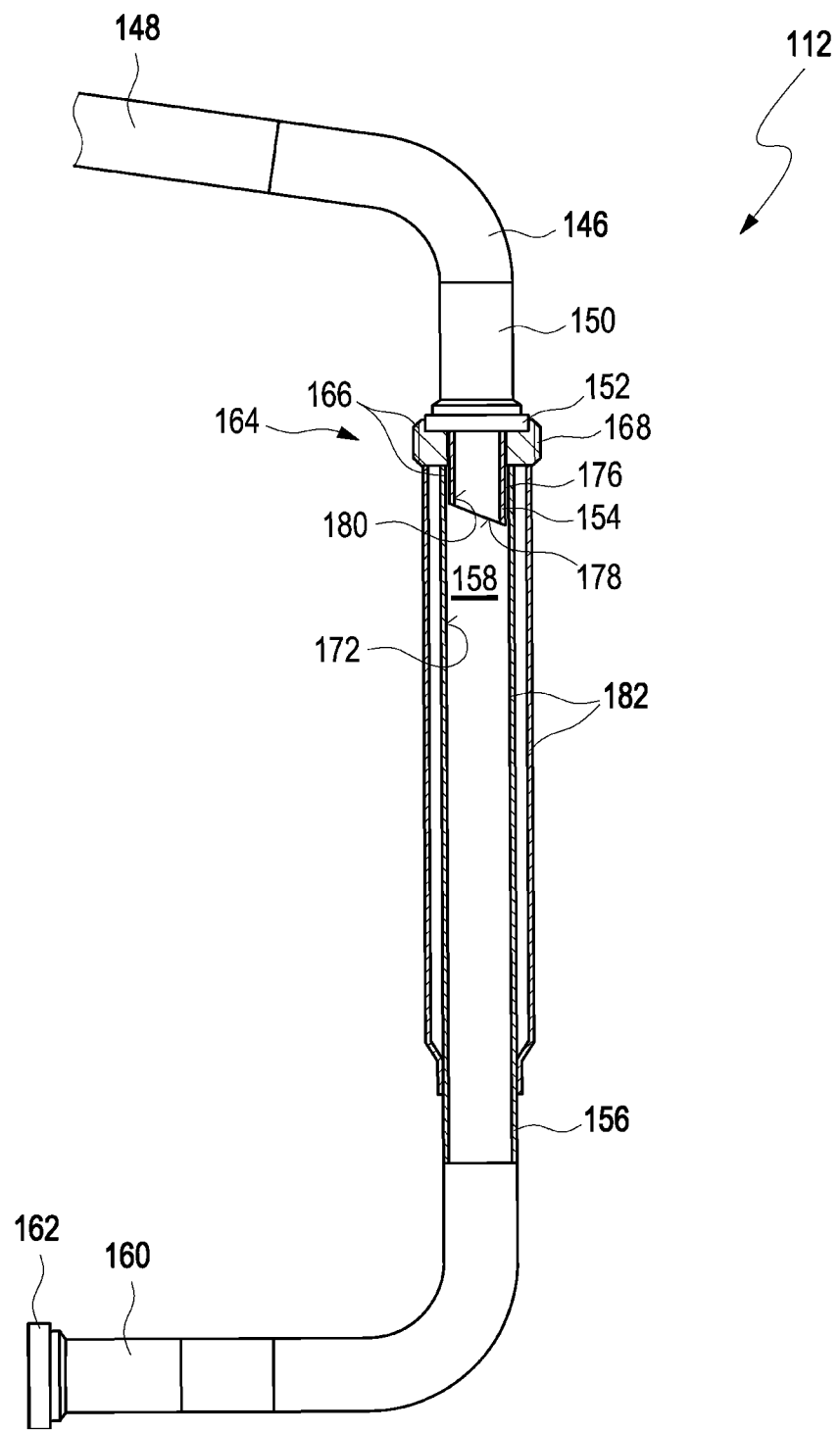
FIG. 2 shows an illustrative embodiment of a removal device.
Figure 3:
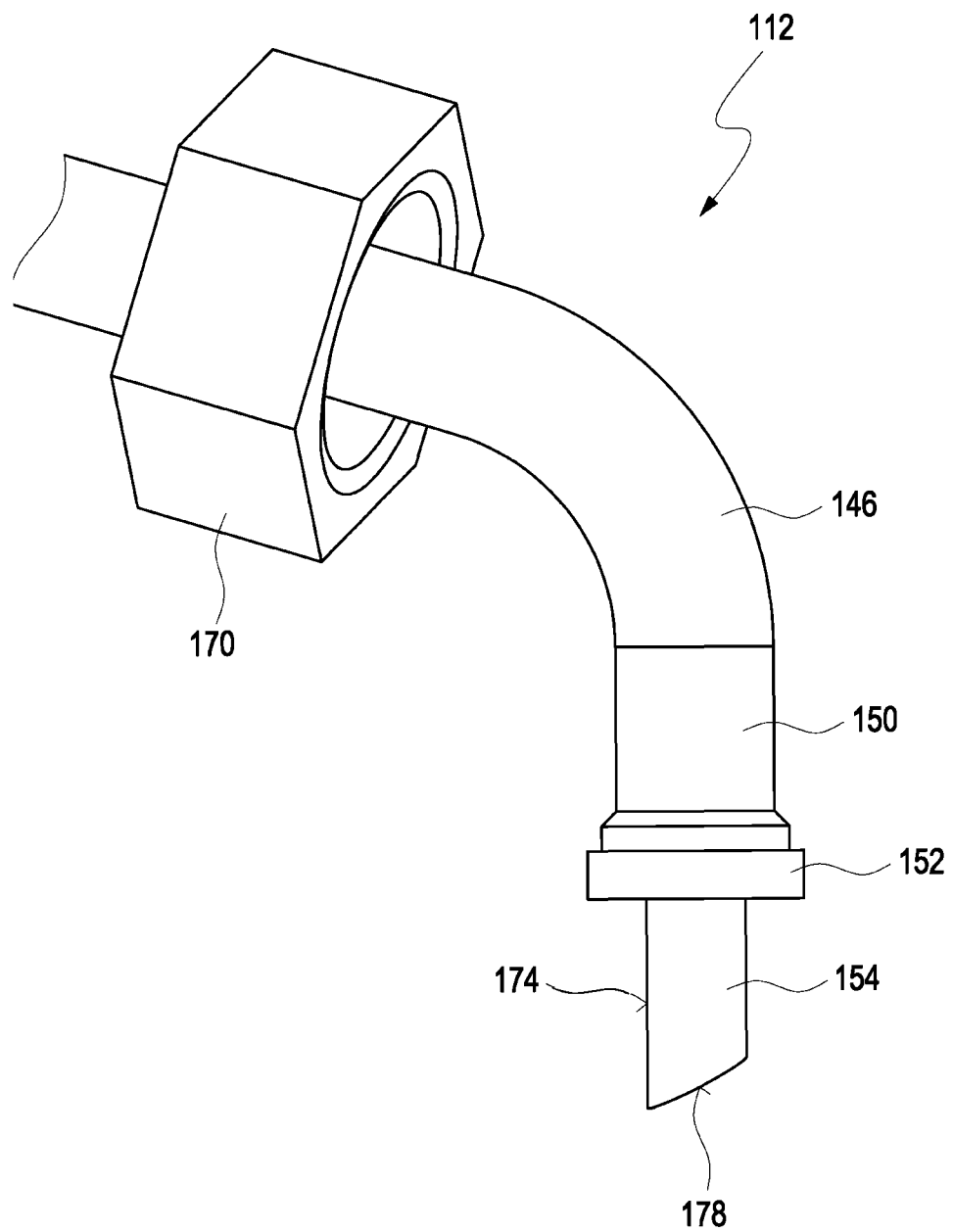
FIG. 3 shows a removal connection piece of the removal device according to FIG. 2.
Figure 4:
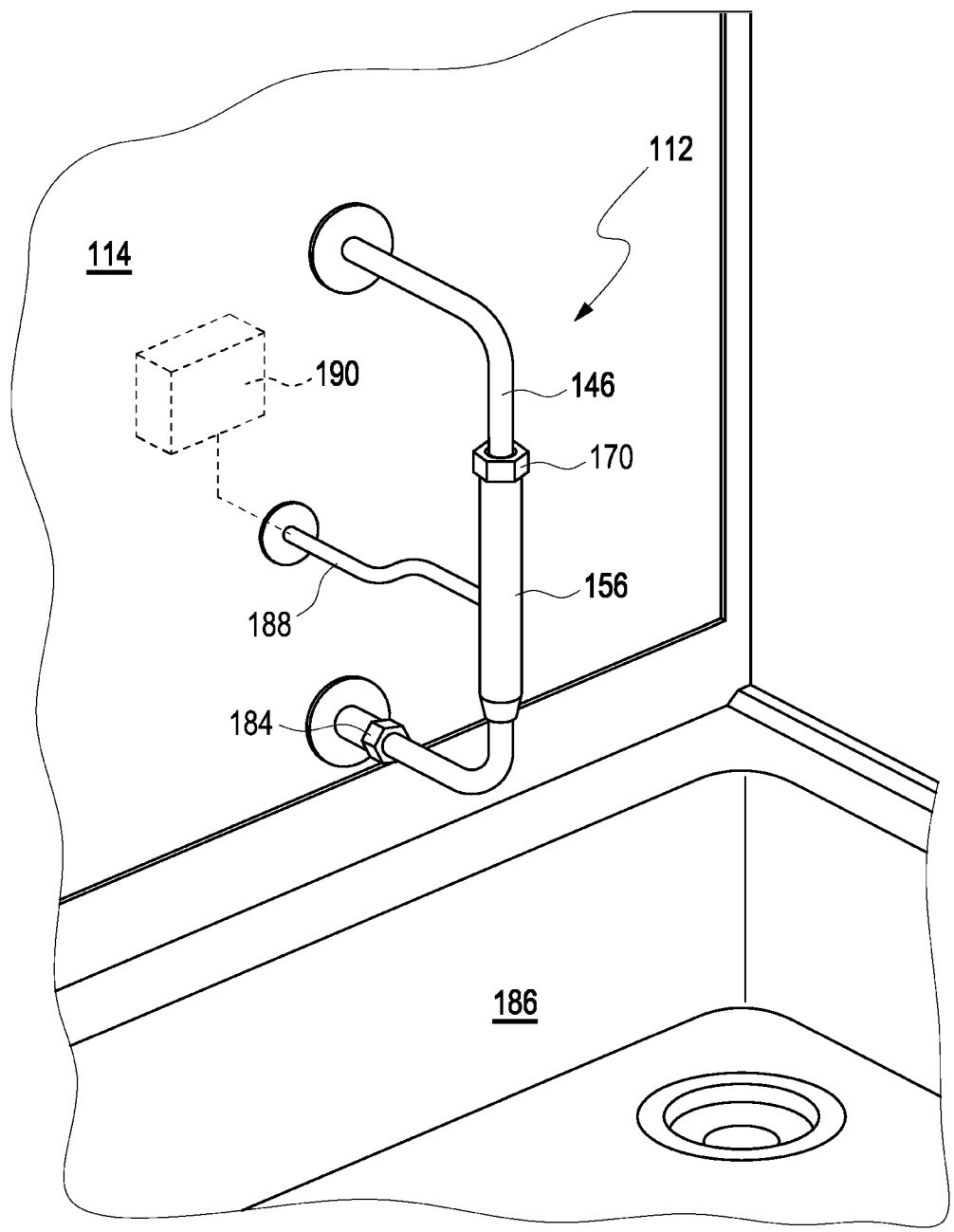
FIG. 4 shows a perspective view of the removal device according to FIG. 2, mounted on a wall.

FIG. 1 is a diagram of the conduit system 110 in one possible configuration. FIGS. 2 to 4 then show details of the removal device 112 in a sectional view (FIG. 2), in a perspective view with the coupling bend removed (FIG. 3), and in a perspective view when mounted on a wall 114 (FIG. 4). The figures are explained jointly hereinbelow.

The conduit system 110 in the view according to FIG. 1 comprises a container 116 for receiving the low-germ liquid, also referred to simply as the WFI container in connection with WFI. This container 116 is filled with the low-germ liquid via a supply line (not shown in detail), for example, from a preparation device.

The container 116 is incorporated in a pipe system 118. The low-germ liquid can be pumped in this pipe system in particular in a circulation, wherein a flow direction is indicated symbolically in FIG. 1 by reference number 120. The circulation can in particular be maintained by a pump 122 which removes low-germ liquid from the container 116 via a removal conduit 124, pumps this low-germ liquid through the pipe system 118 and then returns it to the container 116 via a feed conduit 126, which opens out, for example, in a spray nozzle.

To remove the low-germ liquid from the pipe system 118, the conduit system 110 can in particular have at least one branch 128, which can be configured as a T-piece, for example. This branch 128 is connected directly or indirectly to the removal device 112. At least one valve 130, for example, a block valve, can be arranged between the removal device 112 and the branch 128. This at least one valve can, for example, have a first valve 132 for closing the branch 128. Moreover, at least one feed 134 can be provided between the branch 128 and the removal device 112 and can open into a connection between the removal device 112 and the branch 128. This feed 134 can be closable by a second valve 136. This second valve 136 can be combined with the first valve 132 to form the valve 130, for example, the block valve, although it can also be configured separately from the first valve 132.

The removal device 112, which is connected at one end to the branch 128 and is described in more detail below, is provided on a side 138 of the wall 114 that faces away from the pipe system 118 and that can also be designated as a user side. At its opposite end, the removal device 112 can be connected to an outflow 142, again via a valve 140 for example. Moreover, at least one condensate discharge 144 can be provided between the valve 140 and the outflow 142.

In FIGS. 2 to 4, possible details of the removal device 112 are shown in a sectional view. The removal device 112 is mounted vertically for example, as shown in FIG. 4, and is approximately U-shaped overall.

The removal device 112 has a removal connection piece 146, which is connected at its upper end 148 to the valve 132 and the branch 128 and can thus be subjected to low-germ liquid. At its lower end 150, the removal connection piece 146 has a flange 152 or collar, to which a tube end 154 is attached. This tube end 154 can be beveled for example, as can be seen in FIGS. 2 and 3, in order to make it easier for drops to run off.

The removal device 112 moreover has a coupling bend 156. This coupling bend 156 can likewise be tubular, for example, and provides a cavity 158 into which the tube end 154 protrudes. The coupling bend 156 can, for example, be L-shaped, like the removal connection piece 146 too, and can be coupled at its lower end 160 to the outflow 142, again via a flange 162 for example. At its upper end 164, the coupling bend 156 can, for example, have an insert 166 with an outer thread 168. This outer thread 168 can be connected to the flange 152, for example, via a union nut 170, which can be seen in FIG. 3.

The tube end 154 protrudes into the cavity 158, which is also designated as the interior. The interior 158 is dimensioned in such a way that an annular gap 176 forms between an inner wall 172 of the coupling bend 156 and an outer face 174 of the tube end 154. Accordingly, the tube end 154 is arranged freely in the interior 158, such that an end face 178, an inner face 180 and the outer face 174 of the tube end 154 are freely accessible to pure steam and can have pure steam circulate around them.

Accordingly, in order to prepare for removal, the first valve 132, for example, can first of all be closed and the second valve 136 opened, such that pure steam can pass into the removal device 112 via the feed 134. In the interior 158 of the coupling bend 156, this pure steam circulates around the tube end 154 and sterilizes the outer face 174, the end face 178 and the inner face 180. The pure steam can then be led off via the valve 140 and the condensate discharge 144.

After sterilization has taken place, the second valve 136 can also be closed and the feed of pure steam thus interrupted. By releasing the union nut 170, the coupling bend 156 can then be detached from the removal connection piece 146, resulting in the state shown in FIG. 3 with the tube end 154 exposed. The valve 132 can then be opened, and low-germ liquid can be removed from the removal connection piece 146.

As is also shown in FIG. 2, the coupling bend 156 can in particular have a thermally insulated design. Thus, the removal connection piece can in particular have a double-walled configuration, as is indicated symbolically by reference number 182 in FIG. 2.

FIG. 4 shows the removal device 112 in a perspective view in a state when mounted on the wall 114. It will be seen here that the flange 162 of the coupling bend 156 can be fixed, for example, likewise via a union nut 184. It will also be seen that a flush basin 186 can be provided, for example, under the removal device 112, in order to collect low-germ liquid running out. It will also be seen that the removal device 112 can moreover have at least one electrical contact 188, which, for example, can be of a rigid configuration and which, for example, can be connectable to a control unit 190 indicated symbolically in FIG. 4. This control unit can be connected, for example, to the valve 130 and optionally also to the valve 140 and can actuate a removal. In particular, application of steam can be controllable by the control unit 190. For example, the control unit 190 can detect whether the electrical contact 188 is coupled up, which only takes place when the coupling bend 156 is located in the mounted state shown in FIG. 4. Only in this state can pure steam be introduced into the coupling bend 156. In this way, the control unit 190 can, for example, prevent operating personnel from being injured by pure steam when the coupling bend 156 is not fitted on the removal connection piece 146.

The removal device 112 can in particular be produced wholly or partially from stainless steel. It is particularly preferable here if there is a particularly low surface roughness, such that it is made difficult for germs to adhere to the surfaces of the stainless steel. For example, the stainless steel can have a surface roughness RA≤0.8 micrometer or RA<0.8 micrometer.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE SIGNS 110 conduit system
112 removal device
114 wall
116 container
118 pipe system
120 flow direction
122 pump
124 removal conduit
126 feed conduit
128 branch
130 valve
132 first valve
134 feed for pure steam
136 second valve
138 user side
140 valve
142 outflow
144 condensate discharge
146 removal connection piece
148 upper end
150 lower end
152 flange
154 tube end
156 coupling bend
158 cavity, interior
160 lower end
162 flange
164 upper end
166 insert
168 outer thread
170 union nut
172 inner wall
174 outer face
176 annular gap
178 end face
180 inner face
182 double-walled configuration
184 union nut
186 flush basin
188 electrical contact
190 control unit

What is claimed is:

1. A method for removing a low-germ liquid from a conduit system having a removal connection piece, a coupling bend detachably connected to the removal connection piece, and a tube end of the removal connection piece protruding into the coupling bend, the method comprising:
   a) introducing pure steam into the coupling bend; and
   b) contacting an inner face, outer face and end face of the tube end with the pure steam for a sufficient time to thereby sterilize the tube end,
   the method further comprising, before step a:
   connecting an electrical contact to the coupling bend;
   connecting the electrical contact to a controller; and
   using the electrical contact and the controller to detect whether the coupling bend is connected to the removal connection piece.

2. The method of claim 1, wherein the pure steam penetrates a gap between the outer wall of the tube end and the inner wall of the coupling bend.

3. The method of claim 1, wherein the pure steam is introduced into the coupling bend through the tube end.

4. The method of claim 1, wherein the pure steam is introduced into the coupling bend through an opening in the coupling bend that is spaced apart from the tube end.

5. The method of claim 1, wherein the conduit system further comprises a low-germ liquid container that holds the low-germ liquid to be removed from the conduit system, the method further comprising:
   (c) causing the low-germ liquid to flow from the low-germ liquid container disposed on one side of a wall to the removal connection piece disposed on the other side of the wall.

6. The method of claim 1, further comprising:
(c) discharging condensation from the pure steam through a condensate discharge disposed on the opposite side of a wall from the coupling bend.

7. A method for removing a low-germ liquid from a conduit system having a removal connection piece, a coupling bend detachably connected to the removal connection piece, and a tube end of the removal connection piece protruding into the coupling bend, the method comprising:
a) introducing pure steam into the coupling bend; and
b) contacting an inner face, outer face and end face of the tube end with the pure steam for a sufficient time to thereby sterilize the tube end, wherein the steam is introduced through the coupling bend and travels from the coupling bend to the tube end and the removal connection piece.

8. The method of claim 7, wherein the pure steam penetrates a gap between the outer wall of the tube end and the inner wall of the coupling bend.

9. The method of claim 7, further comprising, before step a:
connecting an electrical contact to the coupling bend;
connecting the electrical contact to a controller; and
using the electrical contact and the controller to detect whether the coupling bend is connected to the removal connection piece.

10. The method of claim 7, wherein the conduit system further comprises a low- germ liquid container that holds the low-germ liquid to be removed from the conduit system, the method further comprising:
(c) causing the low-germ liquid to flow from the low-germ liquid container disposed on one side of a wall to the removal connection piece disposed on the other side of the wall.

11. The method of claim 7, further comprising:
(c) discharging condensation from the pure steam through a condensate discharge disposed on the opposite side of a wall from the coupling bend.

* * * * *